(12) United States Patent
Tabor

(10) Patent No.: US 8,579,963 B2
(45) Date of Patent: *Nov. 12, 2013

(54) TRANSCATHETER PROSTHETIC HEART VALVE DELIVERY DEVICE WITH STABILITY TUBE AND METHOD

(75) Inventor: Charles Tabor, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 430 days.

This patent is subject to a terminal disclaimer.

(21) Appl. No.: 12/759,394

(22) Filed: Apr. 13, 2010

(65) Prior Publication Data

US 2011/0251683 A1 Oct. 13, 2011

(51) Int. Cl.
*A61F 2/24* (2006.01)

(52) U.S. Cl.
USPC ........................................ 623/2.11; 623/1.11

(58) Field of Classification Search
USPC ......... 606/108, 191, 194, 198, 200; 623/1.11, 623/1.12, 2.11, 2.18
See application file for complete search history.

(56) References Cited

U.S. PATENT DOCUMENTS

| | | | |
|---|---|---|---|
| 5,683,451 A | 11/1997 | Lenker et al. | |
| 5,824,041 A * | 10/1998 | Lenker et al. | 606/195 |
| 5,906,619 A | 5/1999 | Olson et al. | |
| 6,786,918 B1 * | 9/2004 | Krivoruchko et al. | 623/1.11 |
| 2004/0093003 A1 * | 5/2004 | MacKenzie et al. | 606/190 |
| 2004/0147939 A1 * | 7/2004 | Rabkin et al. | 606/108 |
| 2004/0215317 A1 * | 10/2004 | Cummings | 623/1.11 |
| 2005/0090889 A1 * | 4/2005 | Yanuma et al. | 623/1.11 |
| 2005/0240254 A1 * | 10/2005 | Austin | 623/1.11 |
| 2005/0283223 A1 * | 12/2005 | Greenan | 623/1.11 |
| 2006/0095050 A1 * | 5/2006 | Hartley et al. | 606/108 |
| 2006/0265056 A1 | 11/2006 | Nguyen et al. | |
| 2007/0043420 A1 * | 2/2007 | Lostetter | 623/1.11 |
| 2007/0088431 A1 | 4/2007 | Bourang et al. | |
| 2007/0239266 A1 | 10/2007 | Birdsall | |
| 2007/0239269 A1 | 10/2007 | Dolan et al. | |
| 2008/0255651 A1 * | 10/2008 | Dwork | 623/1.11 |
| 2009/0171456 A1 | 7/2009 | Kveen et al. | |
| 2010/0049313 A1 | 2/2010 | Alon et al. | |

FOREIGN PATENT DOCUMENTS

| | | |
|---|---|---|
| WO | WO2005/002466 | 1/2005 |
| WO | WO2008/031103 | 3/2008 |

OTHER PUBLICATIONS http://www.thefreedictionary.com/system, dictionary definition of the word "system", retrieved May 18, 2012.*

* cited by examiner

*Primary Examiner* — Thomas McEvoy
*Assistant Examiner* — David Eastwood

(57) ABSTRACT

A device for percutaneous delivery of a stented prosthetic heart valve. The device includes a sheath, a handle, and an outer stability tube. The sheath includes a distal capsule and a proximal shaft. The handle has a housing maintaining an actuator mechanism that is coupled to the shaft. The actuator mechanism is configured to selectively move the shaft, and thus the capsule, relative to the housing. The stability tube is coupled to the housing and is coaxially received over the shaft such that the shaft is slidable relative to the stability tube. In a delivery state, the capsule encompasses the prosthetic valve. In a deployed state, the capsule is withdrawn from the prosthetic valve. The shaft slides relative to the stability tube in transitioning from the loaded state to the deployed state. When used with an introducer device, the stability tube frictionally isolates the sheath.

19 Claims, 15 Drawing Sheets

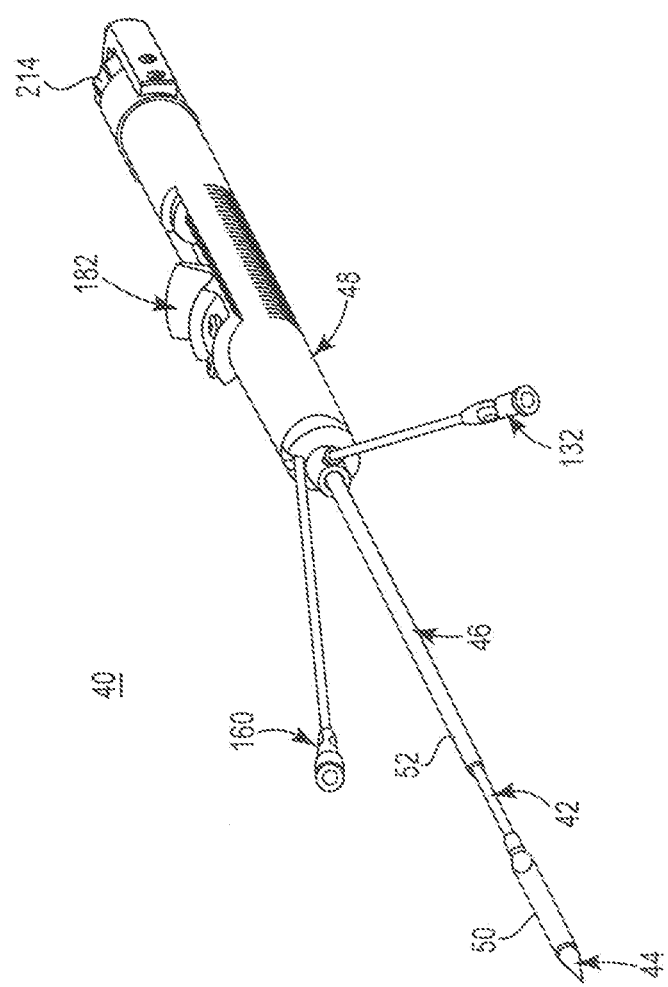

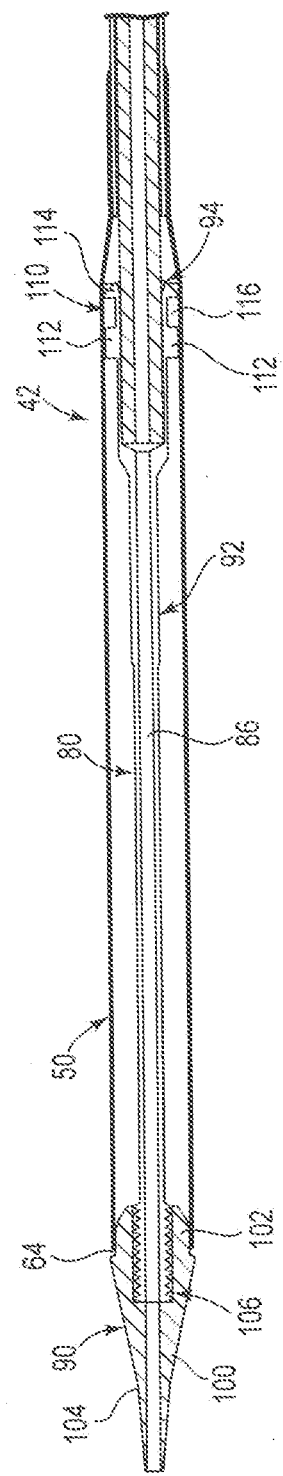

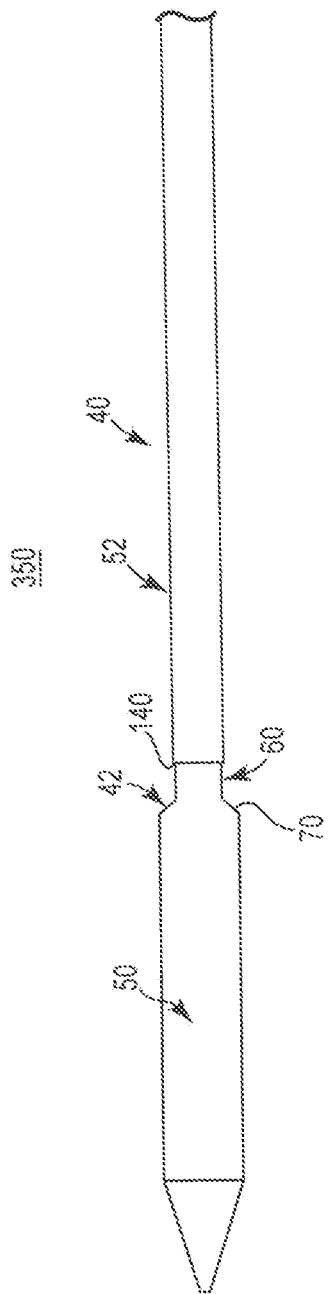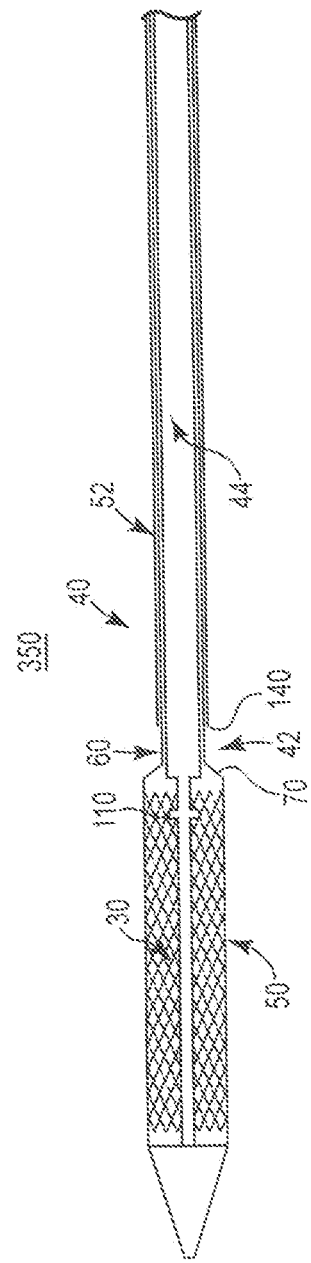

TRANSCATHETER PROSTHETIC HEART VALVE DELIVERY DEVICE WITH STABILITY TUBE AND METHOD

BACKGROUND

The present disclosure relates to systems and methods for percutaneous implantation of a prosthetic heart valve. More particularly, it relates to systems and methods for transcatheter implantation of a stented prosthetic heart valve.

Diseased or otherwise deficient heart valves can be repaired or replaced with an implanted prosthetic heart valve. As used throughout this specification, the terms "repair," "replace," and "restore" are used interchangeably, and reference to "restoring" a defective heart valve is inclusive of implanting a prosthetic heart valve that renders the native leaflets non-functional, or that leaves the native leaflets intact and functional. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as an infection, stroke, renal failure, and adverse affects associated with the use of the heart-lung machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be repaired (e.g., the aortic valve annulus). Although transcatheter techniques have attained widespread acceptance with respect to delivery of conventional stents to restore vessel patency, only mixed results have been realized with respect to percutaneous delivery of the more complex prosthetic heart valve.

Various types and configurations of prosthetic heart valves are available for percutaneous valve replacement procedures, and continue to be refined. The actual shape and configuration of any particular prosthetic heart valve is dependent to some extent upon the native shape and size of the valve being replaced or repaired (i.e., mitral valve, tricuspid valve, aortic valve, or pulmonary valve). In general, prosthetic heart valve designs attempt to replicate the function of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent can be made of a self-expanding material and construction. With these devices, the valved stent is crimped down to a desired size and held in that compressed state within an outer delivery sheath, for example. Retracting the sheath from the valved stent allows the stent to self-expand to a larger diameter, such as when the valved stent is in a desired position within a patient. In other percutaneous implantation systems the valved stent can be initially provided in an expanded or uncrimped condition, then crimped or compressed on a balloon portion of a catheter until it is as close to the diameter of the catheter as possible. Once delivered to the implantation site, the balloon is inflated to deploy the prosthesis. With either of these types of percutaneous stented prosthetic valve delivery devices, conventional sewing of the prosthetic heart valve to the patient's native tissue is typically not necessary.

In addition to the delivery device itself, typical transcatheter heart valve implantation techniques entail the use of a separate introducer device to establish a portal to the patient's vasculature (e.g., femoral artery) and through which the prosthetic valve-loaded delivery device is inserted. The introducer device generally includes a relatively short sheath and a valve structure. By inserting the prosthetic heart valve-loaded sheath through the introducer valve and sheath, a low friction hemostasis seal is created around the outer surface of the delivery sheath. While highly desirable, friction between the introducer device and the delivery sheath can be problematic, leading to unexpected movement of the prosthesis prior to release from the delivery device.

In particular, with a self-expanding stented prosthetic heart valve, the outer delivery catheter or sheath is retracted from over the prosthesis, thereby permitting the stented valve to self-expand and release the prostheses from the delivery device. Friction between the introducer device and the delivery sheath has a tendency to resist necessary proximal movement of the delivery sheath. Because the retraction force is initiated at a handle of the delivery device, this resistance is transferred to the handle. As a result, unless the clinician (and/or an assistant) carefully holds both the handle and the introducer device in a fixed position relative to one another throughout the deployment operation, the handle has a tendency to draw forward. This movement, in turn, is transferred onto the delivery device component (e.g., an internal shaft) otherwise coupled to the loaded prosthetic heart valve, potentially moving the internal component (including the loaded prosthetic heart valve) forward or distally within the patient. While unintended, even a slight displacement from the expected deployment location of the prosthesis relative to the native annulus can lead to severe complications as the prosthesis must intimately lodge and seal against the native annulus for the implantation to be successful. If the deployed prosthesis is incorrectly positioned relative to the native annulus, the deployed stented valve may leak or even dislodge from the implantation site.

For example, FIG. 1A illustrates, in simplified form, an introducer device 10 establishing a portal to a patient's vasculature 12, and through which a prosthetic heart valve-loaded delivery shaft 14 (the tip of which is visible in FIG. 1A) has been inserted. As shown, the delivery shaft 14 has been manipulated to locate the loaded prosthetic heart valve 16 (referenced generally) in a desired position relative to an aortic valve 18. An outer delivery sheath 20 contains the prosthesis 16. Thus, in the state of FIG. 1A, the prosthetic heart valve 16 is properly positioned for deployment from the delivery shaft 14 upon proximal retraction of the delivery sheath 20 relative thereto, with a spacing S being established between a distal end of the delivery device's handle 22 and the introducer device 10. As shown in FIG. 1B, an actuator 24 of the handle 22 is moved by the clinician in an attempt to proximally pull or retract the delivery sheath 20 and release the prosthesis 16. Frictional interface between the delivery sheath 20 and the introducer device 10 may resist proximal movement of the delivery sheath 20 (conventionally, the introducer device 10 is held stationary). As a result, the handle 22 is instead pulled forward toward the introducer device 10 (reflected in FIG. 1B by a decrease in the spacing S). In effect, the handle 22 is being advanced over the delivery sheath 20 rather than the delivery sheath 20 being retracted into the handle 22. Forward movement of the handle 22 is, in turn, directed onto the delivery shaft 14, causing the delivery shaft 14 to distally advance (represented by the arrow B in FIG. 1B) and displace the deploying prosthetic heart valve 16 from the desired valve implantation site 18. While it may be possible to provide an additional isolation layer between the introducer device 10 and the delivery sheath 20, distinct constraints render implementation of an additional layer highly problematic. For example, the tortuous nature of the patient's vasculature necessitates that the delivery device have as low a profile as possible, thereby limiting an available size of the additional layer. Conversely, any additional layers must account for and facilitate necessary retraction of the delivery sheath 20 during a deployment operation.

In light of the above, although there have been advances in percutaneous valve replacement techniques and devices, there is a continued desired to provide different delivery systems for delivering cardiac replacement valves, and in particular self-expanding stented prosthetic heart valves, to an implantation site in a minimally invasive and percutaneous manner.

SUMMARY

The delivery devices of the present disclosure can be used to deliver replacement valves to the heart of a patient. These replacement heart valves may be configured to provide complementary features that promote optimal placement of the replacement heart valve in a native heart valve, such as the aortic valve, mitral valve, pulmonic valve, and/or tricuspid valve. In some embodiments, the replacement heart valves of the present disclosure are highly amenable to transvascular delivery using retrograde transarterial approach (either with or without rapid pacing). The methodologies associated with the present disclosure can be repeated multiple times, such that several prosthetic heart valves of the present disclosure can be mounted on top of, adjacent to, or within one another, if necessary or desired.

The replacement heart valves that are delivered using the delivery devices and methods of the present disclosure typically include a stent frame to which a valve structure is attached. These stent frames can include a wide variety of structures and features that can be used alone or in combination with features of other stent frames. In particular, these stent frames provide a number of different docking and/or anchoring structures that are conducive to percutaneous delivery thereof. Many of the structures are thus compressible to a relatively small diameter for percutaneous delivery to the heart of the patient, and then are expandable via removal of external compressive forces (i.e., self-expanding stents). The device is delivered by the delivery devices described herein can be used to deliver stents, valved stents, or other interventional devices such as ASD (atrial septal defect) closure devices, VSD (ventricular septal defect) closure devices, or PFO (patent foramen ovale) occluders.

With the above in mind, some aspects in accordance with principles of the present disclosure relate to a delivery device for delivering a prosthetic heart valve to a desired location in a patient. In this regard, the prosthetic heart valve includes a stent frame to which a valve structure is attached. The delivery device includes a delivery sheath assembly, a handle, and an outer stability tube. The delivery sheath assembly defines a lumen, and includes a distal capsule and a proximal shaft. The capsule is configured to compressively contain the heart valve prosthesis. The shaft is coupled to the capsule such that longitudinal movement of the shaft is transferred to the capsule. The handle includes a housing and an actuator mechanism. The housing defines a proximal side and a distal side. The actuator mechanism is maintained by the housing and is coupled to the shaft, with the shaft extending distal the distal side of the housing. Further, the actuator mechanism is configured to selectively move the shaft, and thus the capsule, relative to the housing. The outer stability tube is coupled to the housing and is coaxially received over the shaft such that the shaft is slidable relative to the stability tube. Finally, a distal end of the stability tube terminates proximal the capsule in at least a distal-most arrangement of the delivery sheath assembly. With the above in mind, the actuator mechanism is operable to transition the delivery device from a loaded or delivery state to a deployed state. In the loaded state, the capsule encompasses the prosthetic heart valve. In the deployed state, the capsule is withdrawn from the prosthetic heart valve. In this regard, the shaft slides relative to the stability tube in transitioning from the delivery state to the deployed state. In some embodiments, the delivery device is used in conjunction with an introducer device for delivering the prosthetic heart valve into the patient's vasculature, with the stability tube serving to isolate the delivery sheath from the introducer device.

Yet other aspects in accordance with principles of the present disclosure relate to a system for restoring a heart valve of a patient, and include a delivery device as described above along with a prosthetic heart valve. The prosthetic heart valve has a stent frame and a valve structure attached to the frame and forming at least two valve leaflets. The prosthetic heart valve is self-expandable from a compressed arrangement to a natural arrangement. The system is configured to be transitionable from a loaded condition in which the prosthetic heart valve is retained within the capsule of the delivery sheath assembly and a deployed condition in which the capsule is withdrawn from the prosthetic heart valve to permit the prosthesis to self-expand to the natural arrangement and release from the delivery device. In this regard, the actuator mechanism is configured to effectuate transitioning from the loaded condition to the deployed condition by sliding the delivery sheath assembly relative to the prosthetic heart valve and the outer stability tube.

Yet other aspects in accordance with principles of the present disclosure relate to a method for restoring a defective heart valve of a patient. The method includes receiving a delivery device loaded with a prosthetic heart valve having a self-expanding stent frame to which a valve structure is attached. The delivery device includes a delivery sheath containing the prosthetic heart valve in a compressed arrangement and an outer stability tube coaxially received over the delivery sheath and terminating proximal the prosthetic heart valve. A portal to a bodily lumen of the patient is established by an introducer device including an introducer sheath and a valve. The prosthetic heart valve is inserted into the bodily lumen through the introducer valve while constrained within the delivery sheath. In this regard, hemostasis is established between the introducer valve and the outer stability tube. The delivery device is manipulated to guide the prosthetic heart valve through the patient's vasculature and into the defective heart valve. The delivery sheath is withdrawn from over the prosthetic heart valve, with the delivery sheath sliding relative to the outer stability tube. The prosthetic heart valve is released from the delivery device upon withdrawal of the delivery sheath, and permitted to self-expand into engagement with tissue of the native heart valve. In some embodiments, the method includes the outer stability tube isolating the delivery sheath from the introducer valve such that the delivery sheath does not frictionally interface with the introducer valve.

BRIEF DESCRIPTION OF THE DRAWINGS

FIG. 3 is a perspective view of a percutaneous stented prosthetic heart valve delivery device in accordance with principles of the present disclosure;

FIG. 5A is an enlarged cross-sectional view of a distal portion of the delivery device in a loaded state;

FIG. 9A is a simplified side view of a system for restoring (e.g., replacing) a defective heart valve of a patient, including the prosthetic heart valve of FIG. 2A loaded within the delivery device of FIG. 3 in a delivery state;

FIG. 9B is a simplified cross-sectional view of the system of FIG. 9A;

DETAILED DESCRIPTION

Figure 1A:
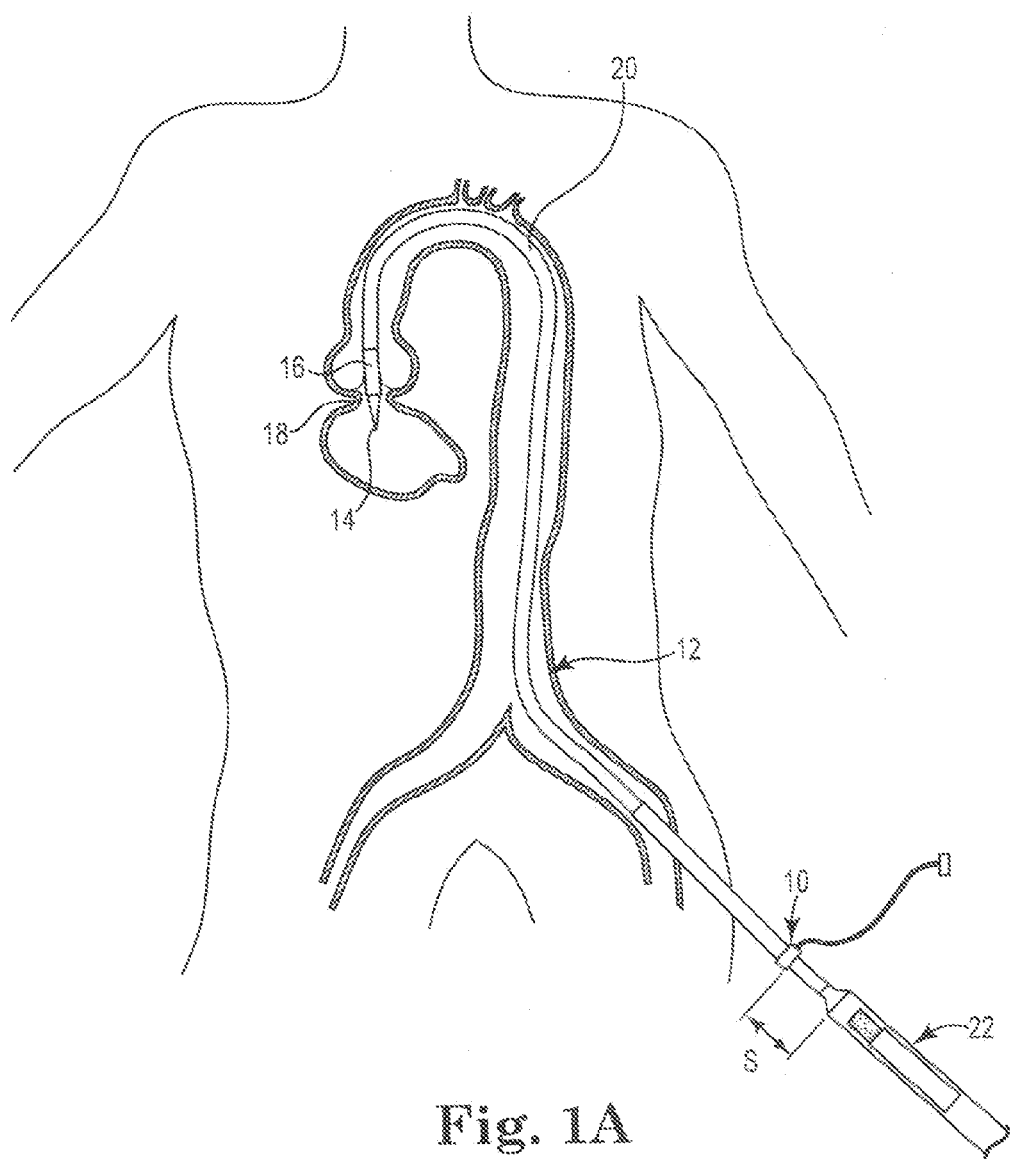
FIGS. 1A and 1B are simplified illustrations of conventional transcatheter delivery and implantation of a stented prosthetic heart valve.
Figure 1B:
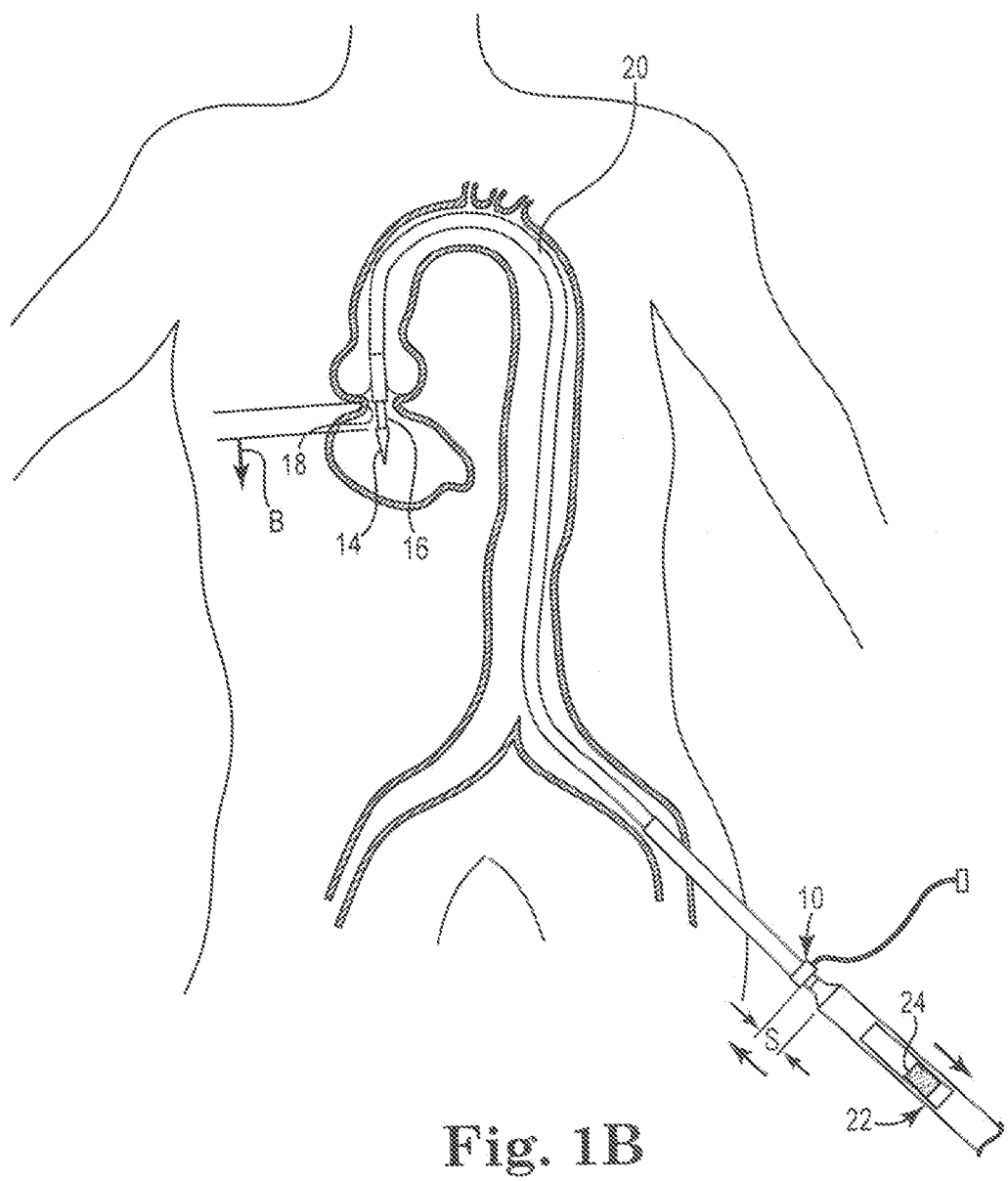

As referred to herein, the stented prosthetic heart valves used in accordance with and/or as part of the various systems, devices, and methods of the present disclosure may include a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace a failed bioprosthesis, such as in the area of an aortic valve or mitral valve, for example.

In general terms, the stented prosthetic heart valves of the present disclosure include a stent maintaining a valve structure (tissue or synthetic), with the stent having a normal, expanded arrangement and collapsible to a compressed arrangement for loading within the delivery device. The stent is normally constructed to self-deploy or expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine pericardial leaflets) and subsequently assembled to the support structure of the stent frame. In another alternative, the stent frame and leaflets can be fabricated at the same time, such as may be accomplished using high-strength nano-manufactured NiTi films produced at Advanced Bioprosthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from the compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached valves can be mounted onto a delivery device. The stent frame support structures are configured so that they can be changed to their normal, expanded arrangement when desired, such as by the relative movement of one or more sheaths relative to a length of the stent frame.

The wires of the support structure of the stent frames in embodiments of the present disclosure can be formed from a shape memory material such as a nickel titanium alloy (e.g., Nitinol). With this material, the support structure is self-expandable from the compressed arrangement to the normal, expanded arrangement, such as by the application of heat, energy, and the like, or by the removal of external forces (e.g. compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 2A:
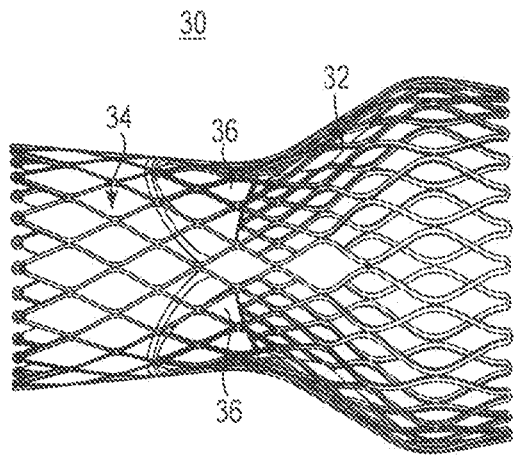
FIG. 2A is a side view of a stented prosthetic heart valve useful with systems, devices, and methods of the present disclosure and in a normal, expanded arrangement.
Figure 2B:
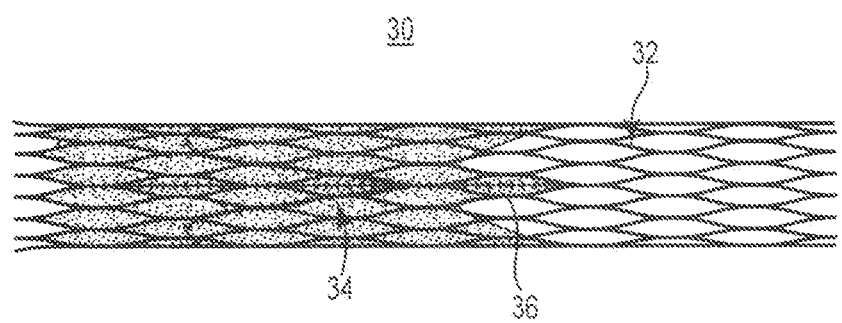
FIG. 2B is a side view of the prosthetic heart valve of FIG. 2A in a compressed arrangement.

With the above understanding in mind, one non-limiting example of a stented prosthetic heart valve 30 useful with systems, devices and methods of the present disclosure is illustrated in FIG. 2A. As a point of reference, the prosthetic heart valve 30 is shown in a normal or expanded arrangement in the view of FIG. 2A; FIG. 2B illustrates the prosthetic heart valve 30 in a compressed arrangement (e.g., when compressively retained within an outer catheter or sheath). The prosthetic heart valve 30 includes a stent or stent frame 32 and a valve structure 34. The stent frame 32 can assume any of the forms described above, and is generally constructed so as to be self-expandable from the compressed arrangement (FIG. 2B) to the normal, expanded arrangement (FIG. 2A). In other embodiments, the stent frame 32 is expandable to the expanded arrangement by a separate device (e.g., a balloon internally located within the stent frame 32). The valve structure 34 is assembled to the stent frame 32 and provides two or more (typically three) leaflets 36. The valve structure 34 can assume any of the forms described above, and can be assembled to the stent frame 32 in various manners, such as by sewing the valve structure 34 to one or more of the wire segments defined by the stent frame 32.

With the but one acceptable construction of FIGS. 2A and 2B, the prosthetic heart valve 30 is configured for replacing or repairing an aortic valve. Alternatively, other shapes are also envisioned, adapted to the specific anatomy of the valve to be repaired (e.g., stented prosthetic heart valves in accordance with the present disclosure can be shaped and/or sized for replacing a native mitral, pulmonic, or tricuspid valve). With the one construction of FIGS. 2A and 2B, the valve structure 34 extends less than the entire length of the stent frame 32, but in other embodiments can extend along an entirety, or a near entirety, of a length of the stent frame 32. A wide variety of other constructions are also acceptable and within the scope of the present disclosure. For example, the stent frame 32 can have a more cylindrical shape in the normal, expanded arrangement.

With the above understanding of the stented prosthetic heart valve 30 in mind, one embodiment of a delivery device 40 in accordance with the present disclosure for percutaneously delivering and implanting the prosthesis 30 is shown in FIG. 3. Although the delivery device 40 can be loaded with the stented prosthetic heart valve 30 (FIGS. 2A and 2B) for delivery thereof to define a system for restoring a defective heart valve, the prosthesis is not shown in FIG. 3 in order to more clearly illustrate the components of the delivery device 40. The delivery device 40 includes a delivery sheath assembly 42, an inner shaft assembly 44 (referenced generally), an outer tube assembly 46, and a handle 48. Details on the various components are provided below. In general terms, however, the delivery device 40 is transitionable from a loaded or delivery state (shown in FIG. 3) in which the stented prosthetic heart valve is contained within a capsule 50 of the delivery sheath assembly 42, to a deployed state in which the capsule 50 is retracted from the prosthetic heart valve, thereby permitting the prosthetic heart valve to self-expand (or alternatively caused to expand by a separate mechanism such as a balloon) and release from the delivery device 40. As part of this transitioning, the delivery sheath assembly 42 is slidable relative to the outer tube assembly 46, and in particular an outer stability tube 52 component thereof. The delivery device 40 can be used with a conventional introducer device (not shown), with the outer stability tube 52 serving to frictionally isolate the delivery sheath assembly 42 from the introducer device. In other embodiments, the delivery device 40 is configured to facilitate user-actuated movement, of the stability tube 52 relative to the delivery sheath assembly 42 and the inner shaft assembly 44, for example as part of a re-capture procedure described below.

Figure 4:
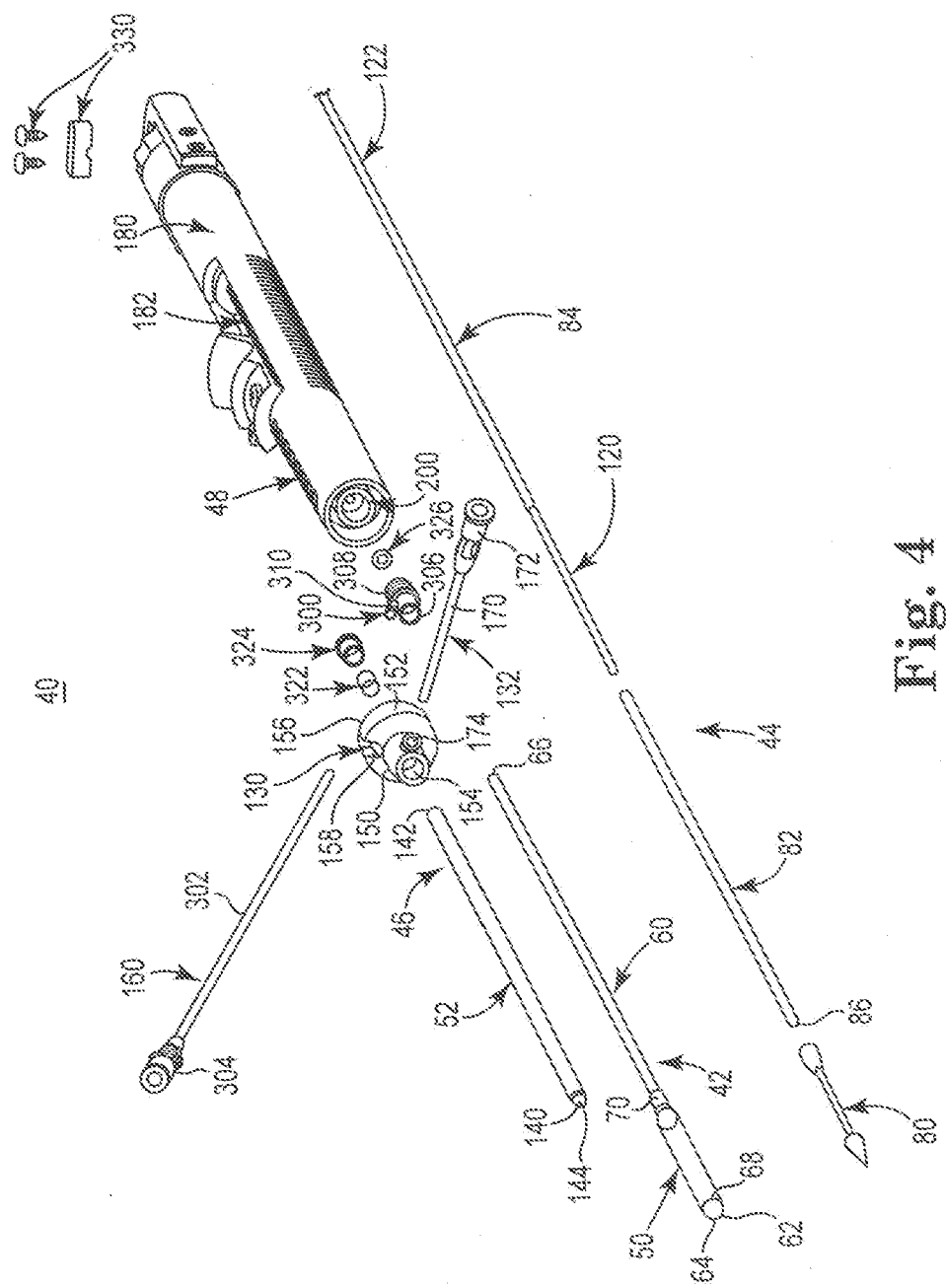
FIG. 4 is an exploded perspective view of the delivery device of FIG. 3.

Components in accordance with some embodiments of the delivery device 40 are shown in greater detail in FIG. 4. As a point of reference, various features of the components 42-48 reflected in FIG. 4 and described below can be modified or replaced with differing structures and/or mechanisms. Thus, the present disclosure is in no way limited to the delivery sheath assembly 42, the inner shaft assembly 44, the outer tube assembly 46, the handle 48, etc., shown and described below. In more general terms, then, delivery devices in accordance with principles of the present disclosure provide features capable of compressively retaining a self-expanding, stented prosthetic heart valve (e.g., the capsule 50), along with one or more components (.e., the outer stability tube 52) capable of isolating the delivery sheath assembly 42 from an introducer device.

In some embodiments, the delivery sheath assembly 42 includes the capsule 50 and a shaft 60, and defines a lumen 62 (referenced generally) extending from a distal end 64 to a proximal end 66. In some constructions, the capsule 50 and the shaft 60 are comprised of differing materials and/or constructions, with the capsule 50 having a longitudinal length approximating (e.g., slightly greater than) a length of the prosthetic heart valve 30 (FIG. 2B) to be used with the device 40. A material and thickness of the capsule 50 is selected to exhibit sufficient radial rigidity so as to overtly resist the expected expansive forces of the prosthetic heart valve 30 when compressed within the capsule 50. However, the capsule 50 exhibits sufficient longitudinal flexibility for ready passage through a patient's vasculature and into a heart valve to be replaced (e.g., retrograde or antegrade approach). For example, the capsule 50 can include a laser-cut metal tube that is optionally embedded within a polymer covering. Alternatively, other constructions are also acceptable, such as a polymer tube that may or may not be embedded with a metal braiding. In other embodiments, the capsule 50 is formed of a transparent material in order to permit a user to see the compressed prosthetic heart valve when loaded therein (and prior to insertion into the patient). Optionally, a radiopaque marker 68 can be assembled to the capsule 50 at or immediately proximal the distal end 64.

The shaft 60 extends proximally from the capsule 50, and can be formed as a braided shaft. Other constructions are also acceptable, with the shaft 60 serving to connect the capsule 50 with the handle 48 as described below. Regardless, the shaft 60 is coupled to the capsule 50 at a connection point 70 (e.g., heat or adhesive bonding) to define a discernable proximal end of the capsule 50, and is constructed to be sufficiently flexible for passage through a patient's vasculature yet exhibits sufficient longitudinal rigidity to effectuate desired axial movement of the capsule 50. In other words, proximal retraction of the shaft 60 is directly transferred to the capsule 50 and causes a corresponding proximal retraction of the capsule 50. In some embodiments, the shaft 60 is configured to transmit a rotational force or movement onto the capsule 50. In other embodiments, the capsule 50 and the shaft 60 can be homogeneously formed as a single, continuous tube or sheath.

The inner shaft assembly 44 can assume a variety of forms appropriate for supporting a stented prosthetic heart valve within the capsule 50. For example, the inner shaft assembly 44 can include a retention member 80, an intermediate tube 82, and a proximal tube 84. In general terms, the retention member 80 is akin to a plunger, and incorporates features for retaining the stented prosthetic heart valve 30 (FIG. 2B) within the capsule 50 as described below. The intermediate tube 82 connects the retention member 80 to the proximal tube 84, with the proximal tube 84, in turn, coupling the inner shaft assembly 44 with the handle 48. The components 80-84 can combine to define a continuous lumen 86 (referenced generally) sized to slidably receive an auxiliary component such as a guide wire (not shown).

One embodiment of the retention member 80 is shown in greater detail in FIG. 5A in conjunction with the capsule 50 of a delivery sheath assembly 42. The retention member 80 can include a tip 90, a support tube 92, and a proximal hub 94. FIG. 5A further reflects the lumen 86 as defined along the retention member 80.

The tip 90 forms or defines a leading nose portion 100 and a trailing shoulder portion 102. The nose portion 100 defines a distally tapering outer surface 104 adapted to promote atraumatic contact with bodily tissue. The shoulder portion 102 is sized to be slidably received within the distal end 64 of the capsule 50 as illustrated. The distal end 64 of the capsule 50 and the shoulder portion 102 are configured to provide a small clearance gap (e.g., on the order of 0.001 inch or greater) to permit free movement of the capsule 50 relative to the tip 90 from the loaded state of FIG. 5A. In some constructions, the shoulder portion 102 can further define an internally threaded bore 106 for threaded coupling with the corresponding feature of the support tube 92.

The support tube 92 is configured to internally support a compressed, stented prosthetic heart valve generally disposed thereover, and has a length and outer diameter corresponding with dimensional attributes of the prosthetic heart valve. While the support tube 92 is illustrated as being threadably coupled to the tip 90, other constructions are also acceptable (e.g., the tip 90 and the support tube 92 can be integrally formed as a homogenous body).

The hub 94 is attached to the support tube 92 opposite the tip 90 (e.g., adhesive bond), and provides an engagement feature 110 (referenced generally) configured to selectively capture a corresponding feature of the prosthetic heart valve. The engagement feature 110 can assume various forms, and in some constructions includes a plurality of circumferentially arranged fingers 112 and a flange 114. The fingers 112 are sized to be received within corresponding apertures formed by the prosthetic heart valve stent frame 32 (FIG. 2A). For example, the prosthetic heart valve stent frame 32 can form wire loops at the proximal end thereof that are releasably received over respective ones of the fingers 112 and nest against the hub 94 when compressed within the capsule 50. The flange 114 is proximally spaced from the fingers 112, with a gap 116 therebetween sized for nested placement of the prosthetic heart valve's proximal end. With this construction, the capsule 50 captures the stent frame within the gap 116 in the loaded or delivery state of FIG. 5A. The fingers 112 and the flange 114 impede distal and proximal movement of the prosthetic heart valve stent frame 32, respectively. In the deployed state of FIG. 5B, the delivery sheath assembly 42 is retracted relative to the retention member 80, with the distal end 64 of the capsule 50 being proximal the flange 114. In this arrangement, then, the prosthetic heart valve stent frame 32 is no longer constrained within the capsule 50 and thus is free to self-expand (or be caused to expand by a separate mechanism such as a balloon) and release from the engagement feature 110. A wide variety of other temporary stent frame engagement feature configurations are also acceptable. For example, the hub 94 can form slots sized to slidably receive a corresponding component of the prosthetic heart valve (e.g., a bar or leg segment of the stent frame). Further, the inner shaft assembly 44 can incorporate additional structures and/or mechanisms that assist in temporarily retaining the prosthetic heart valve (e.g., a tubular segment biased over the engagement structure 96), such as described in U.S. Provisional Application Ser. No. 61/237,373 entitled "Transcatheter Valve Delivery Systems and Methods" filed Aug. 27, 2009 and the entire teachings of which are incorporated herein by reference.

Returning to FIG. 4, the intermediate tube 82 is formed of a flexible material (e.g., PEEK), and is sized to be slidably received within the delivery sheath assembly 42, and in particular the shaft 60.

The proximal tube 84 can include, in some embodiments, a leading portion 120 and a trailing portion 122. The leading portion 120 serves as a transition between the intermediate and proximal tubes 82, 84, and thus can be a flexible tubing (e.g., PEEK) having a diameter slightly less than that of the intermediate tube 82. The trailing portion 122 has a more rigid construction, configured for robust assembly with the handle 48. For example, the trailing portion 122 can be a metal hypotube. In other embodiments, the intermediate and proximal tubes 82, 84 are integrally formed as a single, homogenous tube or solid shaft.

The outer tube assembly 46 can assume various forms and generally includes the outer stability tube 52. In some constructions, the outer tube assembly 46 can further include a cap 130 and a flush port construction 132. As described in greater detail below, the cap 130 rigidly connects the outer stability tube 52 to the handle 48. The flush port construction 132 provides a pathway for fluidly accessing a space between the outer stability tube 52 and the delivery sheath assembly 42.

The outer stability tube 52 serves as a stability shaft for the delivery device 40, and defines a distal end 140, a proximal end 142, and a passageway 144 (referenced generally) extending between, and fluidly open at, the ends 120, 142. The passageway 144 is sized to coaxially receive the delivery sheath assembly 42, and in particular the shaft 60, in a manner permitting sliding of the shaft 60 relative to the outer stability tube 52. Stated otherwise, an inner diameter of the outer stability tube 52 is slightly greater than an outer diameter of the shaft 60. In some constructions, a difference between the outer diameter of the shaft 60 and the inner diameter of the outer stability tube 52 is on the order of 1 French, although other dimensions are also contemplated. Regardless, and as described in greater detail below, the outer stability tube 52 has a length selected to extend over a significant (e.g., at least a majority, in other embodiments approximately 80%) of a length of the shaft 60 in distal extension from the handle 48. Further, the outer stability tube 52 exhibits sufficient radial flexibility to accommodate passage through a patient's vasculature (e.g., the femoral artery).

The optional cap 130 is a hub-like body forming a head 150 and a base 152. The head 150 is configured for attachment to the proximal end 142 of the outer stability tube 52. For example, the head 150 can form a passageway 154 sized to frictionally receive the proximal end 142 of the outer stability tube 52. Additional fixation of the outer stability tube 52 with the head 150 can be provided (e.g., adhesive, weld, etc.). The base 152 is configured for rigid attachment to the handle 48 as described below. For example, in some constructions, the base 152 can form a stepped ring 156 (referenced generally) configured to connect with a corresponding feature of the handle 48. The base 152 can further form a channel 158 sized to slidably receive a component of an optional purge port construction 160 provided with the handle 48. Alternatively, the cap 130 can assume a variety of other forms, and the outer stability tube 52 can be coupled to the handle 48 in a variety of differing manners that may or may not include the cap 130.

The optional flush port construction 132, where provided, includes tubing 170 and a port connector 172. The tubing 170 is fluidly connected to the passageway 154 of the cap 130 via a radial hole 174 formed in the head 150. The port connector 172 is fluidly connected to the tubing 170 and can assume a variety of forms appropriate for establishing a selective fluid connection to the tubing 170. For example, in some constructions, the port connector 172 is a luer lock-type structure. In other embodiments, the flush port construction 132 can be eliminated.

The handle 48 generally includes a housing 180 and an actuator mechanism 182 (referenced generally). The handle 48 can optionally include additional components, such as the purge port assembly 160. Regardless, the housing 180 maintains the actuator mechanism 182, with the handle 48 configured to facilitate sliding movement of the delivery sheath assembly 42 relative to the outer stability tube 52 and the inner shaft assembly 44 as described below.

Figure 6:
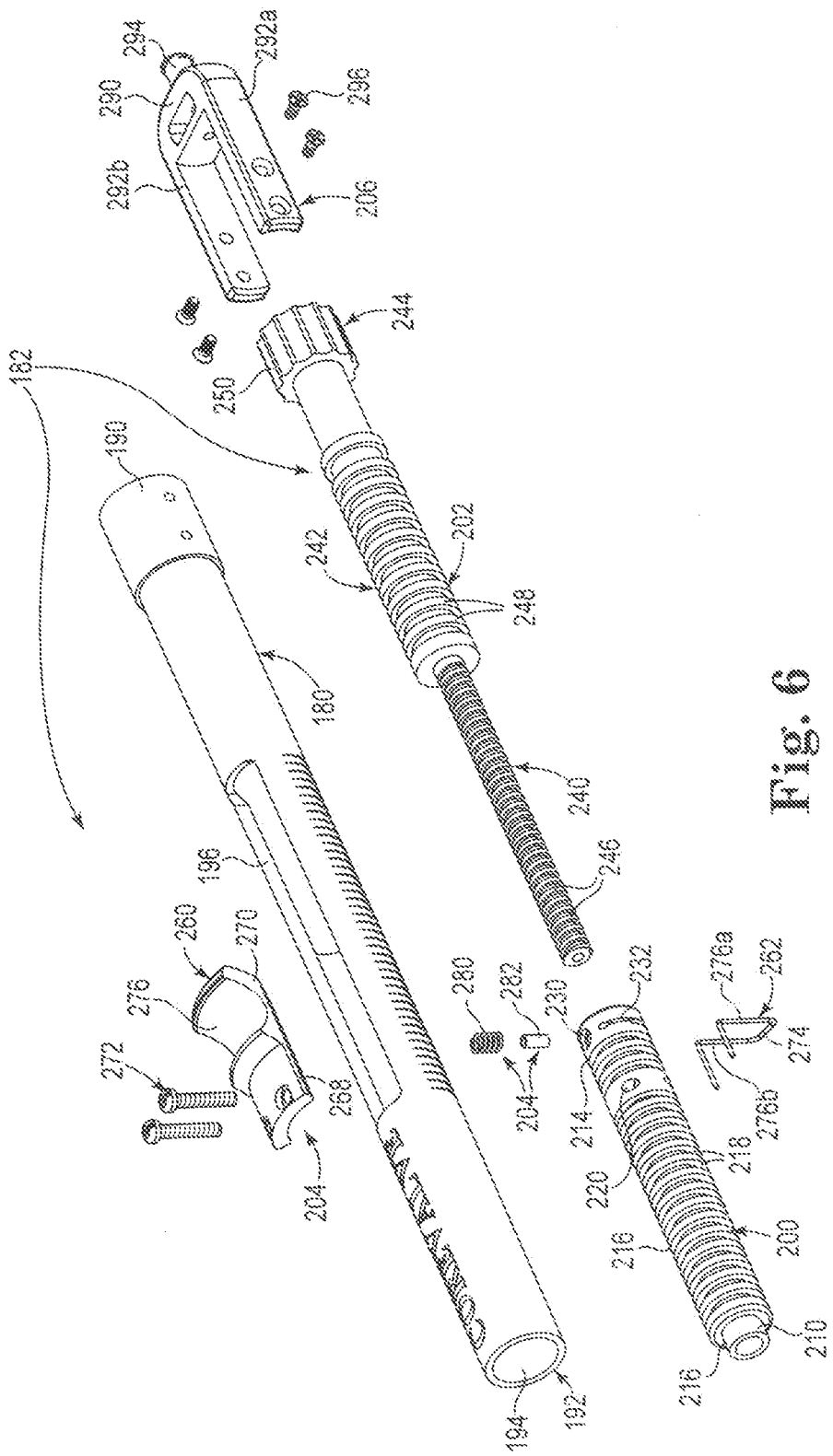
FIG. 6 is an exploded perspective view of a handle portion of the delivery device of FIG. 3.

One optional construction of the housing 180 and the actuator mechanism 182 is shown in greater detail in FIG. 6. The housing 180 provides a surface for convenient handling and grasping by a user, and can have the generally cylindrical shape as shown. A wide variety of other shapes and sizes are appropriate for user handling also contemplated. Regardless, the housing 180 forms or defines a proximal side 190 and a distal side 192. The housing 180 is further configured to maintain portions of the actuator mechanism 182, for example within an open interior 194 defined by the housing 180. In some constructions, the housing 180 further forms a longitudinal slot 196 that is open to the interior 194 and through which the actuator mechanism 182 extends for interfacing by a user.

The actuator mechanism 182 is generally constructed to provide selective retraction (and optionally advancement) of the delivery sheath assembly 42 (FIG. 4), and can have a variety of constructions and/or devices capable of providing the desired user interface. In the but one acceptable configuration of FIG. 6, the actuator mechanism 182 includes a sheath connector body 200, a drive body 202, an actuator assembly 204 (referenced generally), and a stirrup 206. In general terms, the sheath connector body 200 is configured for assembly to the delivery sheath assembly 42 (FIG. 4), with the actuator assembly 204 selectively locking a longitudinal position of the sheath connector body 200 relative to the drive body 202 as part of a sheath movement operation. The stirrup 206 facilitates insertion and removal of a separate component (e.g., a guide wire) relative to the delivery device 40 (FIG. 3).

The sheath connector body 200 has a tubular construction, defining or forming a leading portion 210, an intermediate portion 216, and a trailing portion 214. The leading portion 210 is configured for fixed connection with the delivery sheath assembly 42 (FIG. 4), and can form a rim 216 sized to receive a corresponding component otherwise interconnected to the delivery sheath assembly 42 as described below. The intermediate portion 212 is sized to slidably nest within the interior 194 of the housing 180, and can optionally form circumferential recesses 218 as shown to better promote sliding of the sheath connector body 200 relative to the housing 180 (i.e., the recesses 218 reduce frictional contact between the sheath connector body 200 and the housing 180). Further, the intermediate portion 212 is configured for coupling with a component of the actuator assembly 204 as described below, and thus can include one or more threaded bores 220.

The trailing portion 214 is configured for connection to the actuator assembly 204, as well as to facilitate selective interface between the actuator assembly 204 and the drive body 202. For example, in some embodiments, the trailing portion 214 forms a radial hole 230 and a circumferential slot 232 for reasons made clear below.

The drive body 202 has a tubular construction, and forms or defines a screw region 240, a support region 242, and a control knob 244. The screw region 240 has an outer diameter sized to be coaxially received within the sheath connector body 200. Further, an exterior surface of the screw region 240 forms a helical groove 246.

The support region 242 extends proximally from the screw region 240, and has an enlarged diameter. More particularly, the support region 242 is sized in accordance with an inner diameter of the housing 180, selected to rotatably support the drive body 202 within the housing interior 194. In some constructions, the support region 242 can form circumferential recesses 240 as shown for better promoting rotation of the drive body 202 relative to the housing 180 where desired (i.e., the surface area of contact between the support region 242 and the housing 180 is reduced due to presence of the recesses 248 such that a frictional resistance to rotation of the drive body 202 is also reduced).

The control knob 244 extends proximally from the support region 242, and provides a structured surface 250 adapted to facilitate user handling. In particular, the control knob 244 is configured to promote user-directed rotation of the drive body 202 as described below.

The actuator assembly 204 includes, in some constructions, a user interface body 260, a locking body 262, and a biasing device 264. The user interface body 260 can assume various shapes and sizes appropriate for promoting desired handling thereof by a user. For example, in some constructions, the user interface body 260 is a cursor-type body providing a contoured external surface 266 shaped to receive a user's thumb. Other shapes differing from those reflected in FIG. 6 are also acceptable. The interface body 260 can be viewed as defining a leading section 268 and a trailing section 270, with the leading section 268 being attached to the sheath connector body 200, and in particular the intermediate portion 212, for example by one or more couplers (e.g., screws) 272 connected to the user interface body 260 and secured within the bores 220 of the sheath connector body 200. Upon final assembly, the user interface body 260 is longitudinally slidable relative to the housing 180, and thus can have an interior contour matching an external shape or curvature of the housing 180.

The locking body 262 is configured to selectively couple or lock the sheath connector body 200 relative to the drive body 202. For example, in some constructions, the locking body 262 is a wire shaped to define a central segment 274 and opposing arms 276a, 276b. The wire 262 has a diameter slightly less than a width of the slot 232 in the trailing portion 214 of the sheath connector body 200. Thus, the wire 262 can slidably nest within the slot 232, with the central segment 274 selectively moving within the slot 232, into and out of engagement with the helical groove 246 of the drive body 202 upon final assembly. The arms 276a, 276b are configured for coupling with the trailing section 270 of the user interface body 260, and have a length appropriate for engagement and release of the central segment 274 with the helical groove 246 depending upon a spatial position of the user interface body 260 as described below.

The biasing device 244 includes a spring 280 and a support pin 282. The spring 280 is assembled between the sheath connector body 200 and the user interface body 260, and serves to bias the trailing section 270 of the user interface body 260 away from the sheath connector body 200. For example, the spring 280 can be secured within the hole 230 of the sheath connector body 200, with the support pin 282 maintaining the spring 280 relative to the bodies 200, 260.

The optional stirrup 206 includes a guide piece 290 and opposing legs 292a, 292b. The guide piece 290 forms a port 294 through which an auxiliary component (e.g., a guide wire) can be inserted and supported. The legs 292a, 292b, project from the guide piece 290, and are configured for assembly to the proximal side 190 of the housing 180, for example via connectors (e.g., screws) 296.

Returning to FIG. 4, the optional purge port assembly 160 can include a mounting boss 300, tubing 302, and a port connector 304. The mounting boss 300 is configured to couple the shaft 60 of the delivery sheath assembly 42 with the sheath connector body 200. For example, the mounting boss 300 forms a primary lumen 306 having a diameter approximating an outer diameter of the shaft 60 such that the proximal end 66 of the shaft 60 can be mounted within the primary lumen 306. A rear portion 308 of the mounting boss 300 is configured for coupling with the sheath connector body 200 as described below, and optionally includes external threads. Finally, the mounting boss 300 can form a side port 310 sized for attachment to the tubing 302, with the side port 310 defining a secondary lumen (not shown) that is fluidly open to the primary lumen 306.

The tubing 302 can have a flexible construction (e.g., Pebax® material), and is adapted for attachment to the side port 310 of the mounting boss 300. The port connector 304 is attached to the tubing 302, and can be configured to provide selective fluid connection with the tubing 302. For example, in some constructions, the port connector 304 is a luer lock-type body.

Figure 5B:
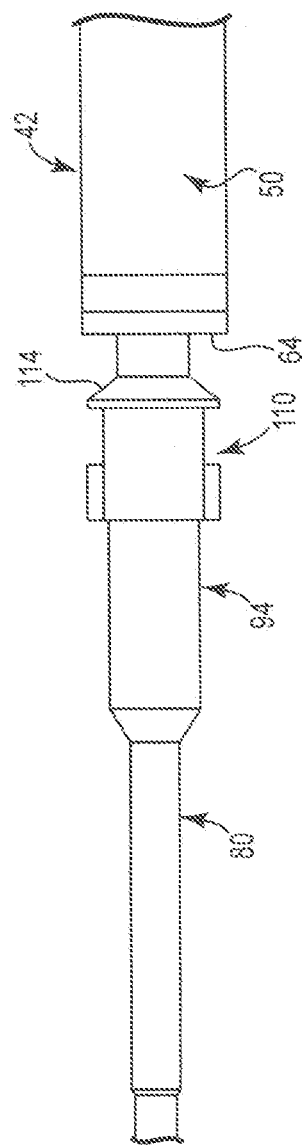
FIG. 5B is an enlarged side view of the distal portion of FIG. 5A in a deployed state.
Figure 7:
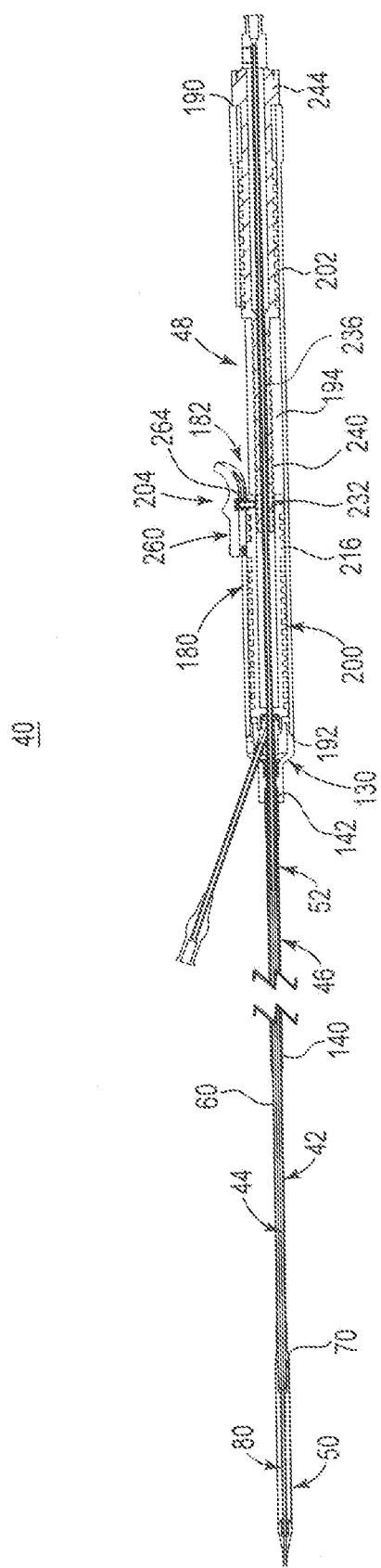
FIG. 7 is a cross-sectional view of the delivery device of FIG. 3.

Construction of the delivery device 40 is reflected in FIG. 7, and includes the delivery sheath assembly 42 being coaxially and slidably disposed between the inner shaft assembly 44 and the outer stability tube 52. As a point of reference, FIG. 7 reflects the delivery device 40 in the delivery state. As shown, the capsule 50 is coaxially disposed over the retention member 80. Each of the assemblies 42-46 are connected to the handle 48, with the inner support assembly 44 and the outer tube assembly 46 being rigidly coupled to the housing 180. The delivery sheath assembly 42 is movably connected to the housing 180 via the actuator mechanism 182 as described below. Generally speaking, then, the delivery sheath assembly 42 can be retracted in a proximal direction relative to the inner and outer assemblies 44, 46 and the housing 180 from the loaded or delivery state of FIG. 7 to the deployed state (FIG. 5B). Regardless, the outer stability tube 52 extends distally from the distal side 192 of the housing 180, and encompasses at least a majority of a length of the shaft 50. In some constructions, however, the outer stability tube 52 terminates proximal the capsule 50 in at least the delivery state. As shown in FIG. 7, the distal end 140 of the outer stability tube 52 is proximal the capsule 50. Further, in some constructions, a length of the outer stability tube 52 in distal extension from the housing 180 is selected to be at least slightly proximal the capsule 50 in the deployed state such that the capsule 50 does not contact the distal end 140 of the outer stability tube 52, or otherwise enter the outer stability tube 52, in transitioning from the delivery state to the deployed state. As a point of reference, the distance of travel of the delivery sheath assembly 42 in transitioning from the delivery state to the deployed state is a function of a length of the selected prosthetic heart valve 30 (FIGS. 2A and 2B). For example, the distance of travel is slightly greater than a longitudinal length of the prosthetic heart valve 30 such that in the deployed state, the capsule 50 is free of the prosthetic heart valve 30. The distal end 140 of the outer stability tube 52 is thus located, in the delivery state, proximally along a length of the shaft 60 at a distance from the capsule 50 (and in particular the connection 70) commensurate with (e.g., slightly greater than) the expected length of travel. For example, with constructions in which the capsule 50, and thus the delivery sheath assembly 42, is retracted a distance of 8 cm in transitioning from the loaded state to the deployed state, the distal end 140 of the stability tube 52 is optionally located a distance in the range of 3-13 cm, optionally approximately 8 cm, proximal of the connection point 70 in the loaded state of FIG. 7. Other dimensional relationships between the length of extension of the outer stability tube 52 relative to the length of the delivery sheath assembly 42 are also envisioned. In some embodiments, however, the outer stability tube 52 extends over, and thus stabilizes, as much of the shaft 60 as possible but does impede sliding/transitioning of the capsule 50 from the delivery state to the deployed state.

Figure 8A:
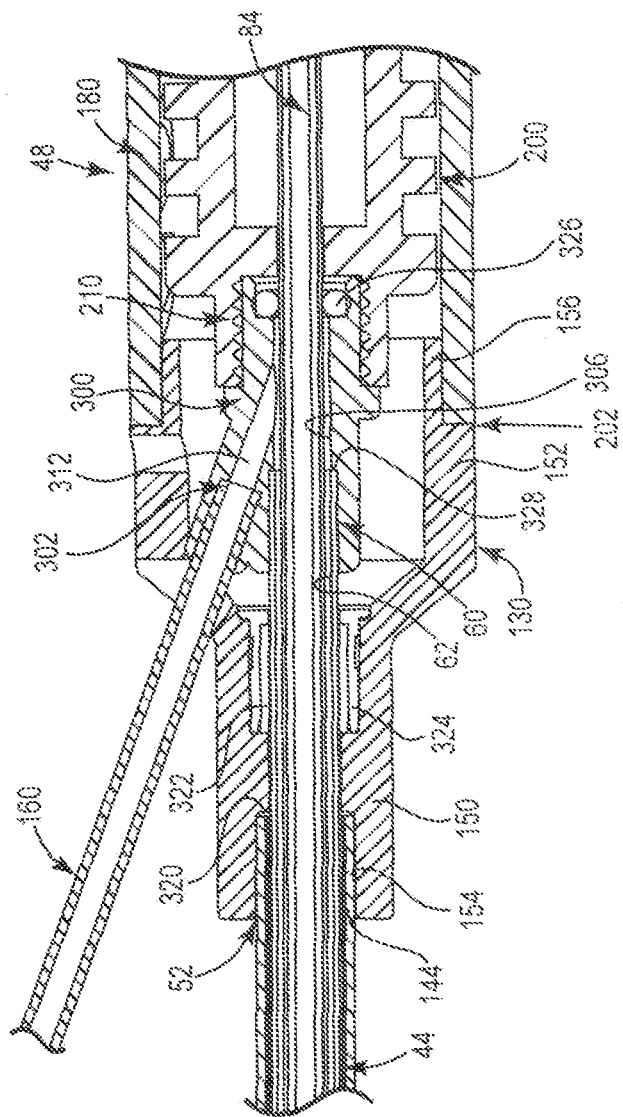
FIG. 8A is an enlarged cross-sectional view of a portion of the delivery device of FIG. 3, illustrating assembly of the handle to various components.

As generally reflected in FIG. 7, the proximal end 142 of the outer stability tube 52 is rigidly coupled to the housing 180 via the cap 130. For example, as shown in FIG. 8A, the proximal end 142 is affixed within the passage 154 of the head 150. Where desired, an adhesive can be employed to effectuate a more robust bond between the outer stability tube 52 and the head 150. The base 152 of the cap 130 is coupled to the distal side 192 of the housing 180. For example, in some constructions, the stepped ring 156 abuts the distal side 192, and is affixed relative thereto. An adhesive can further be utilized to bond the cap 130 to the housing 180. Other mounting constructions are also acceptable and can include, for example, frictional fit, threaded attachment, etc. FIG. 8A further reflects the mounting boss 300 disposed within the cap 130, and coupled to the leading portion 210 of the sheath connector body 200 (e.g., a threaded coupling). The shaft 60 extends within the cap 130, and is coupled to the mounting boss 300 (e.g., an adhesive bond). With this construction, the lumen 62 of the delivery sheath assembly 42 is fluidly open to the primary lumen 306 of the mounting boss 300. The secondary lumen 312 is also fluidly open to the primary lumen 306, with FIG. 8A reflecting a fluid connection being established between the purge tubing 302 and the primary lumen 306 via the secondary lumen 312. Regardless, a gap 320 is established between an inner diameter of the outer stability tube 52 and an outer diameter of the shaft 60 as described above. Though not visible in the view of FIG. 8A, the flush port construction 132 (FIG. 4) is fluidly connected with the gap 320 via the cap 130 as described above. Optionally, a seal 322 and a retainer 324 can be provided to fluidly isolate the gap 320.

The inner shaft assembly 44, and in particular the proximal tube 84, extends within the lumen 62 of the shaft 60 and through the mounting boss 300 and the sheath connector body 200. An O-ring 326 can be assembled over the proximal tube 84 as shown, and serves to fluidly close the primary lumen 306. With this construction, then, the purge tubing 302 is fluidly open to a spacing 328 between an interior of the shaft 60 and an exterior of the proximal tube 84, with the O-ring 326 fluidly closing the spacing 328 relative to the handle 48. Thus, the purge port assembly 160 can be utilized to effectuate fluid transfer (fluid delivery or vacuum) within an interior of the capsule 50 (FIG. 7).

Figure 8B:
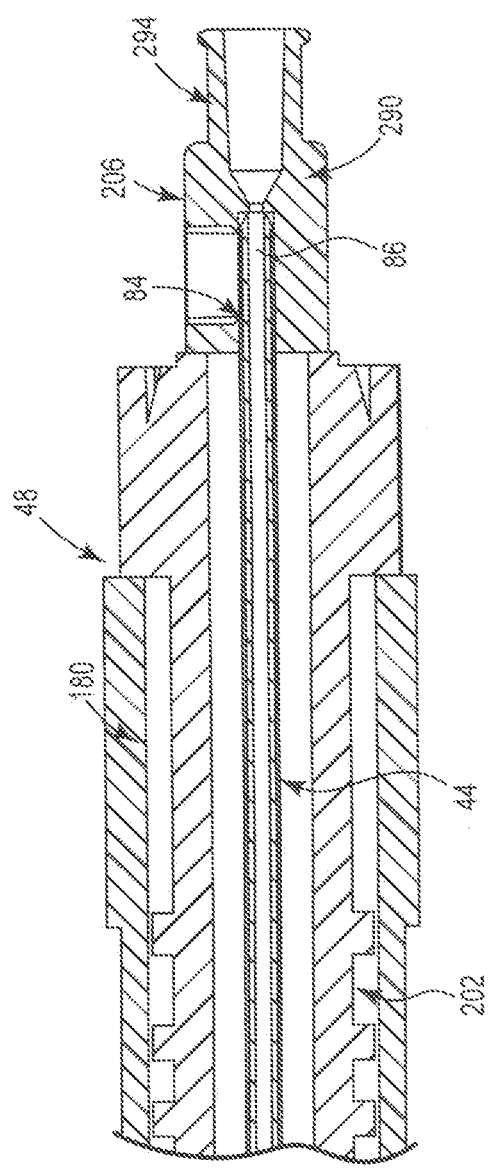
FIG. 8B is an enlarged cross-sectional view of a portion of the delivery device of FIG. 3, illustrating assembly of a distal region of the handle.

The proximal tube 84 of the inner shaft assembly 44 extends proximally through the handle 48, including coaxially through the drive body 202 as shown in FIG. 8B. The proximal tube 84 is assembled to, and supported by, the stirrup 206. In this regard, the port 294 of the guide piece 290 is fluidly connected to the lumen 86 of the proximal tube 84, such that an auxiliary component (e.g., guide wire) inserted through the port 294 is directly guided into the inner shaft assembly lumen 86. In some embodiments, the handle 48 can optionally further include a clamp device 330 (FIG. 4) utilized to secure the proximal tube 84 to the stirrup 206, although other mounting arrangements are also acceptable. Regardless, the stirrup 206 is fixed to the housing 180 such that by mounting the proximal tube 84 to the stirrup 206, the inner shaft assembly 44 is also fixed relative to the housing 180.

Returning to FIG. 7, assembly of the handle 48 generally includes the sheath connector body 200 and the drive body 202 being disposed within the open interior 194 of the housing 180. The screw region 240 of the drive body 202 is slidably received within the sheath connector body 200, with the sheath connector body 200 being slidable over the screw region 240 (and within the housing 180). The drive body 202 is located such that the control knob 244 is proximal the proximal side 190 of the housing 180. With this construction, the drive body 202 is prevented from sliding relative to the housing 180, but is allowed to rotate relative thereto. The actuator assembly 204 selectively links the sheath connector body 200 with the drive body 202. In particular, the user interface body 260 is coupled to the intermediate portion 212 of the sheath connector body 200 as described above, and is biased to the raised position of FIG. 7 by the biasing device 264. In this raised position, the locking body 262 (best shown in FIG. 6) extends through the slot 232 in the sheath connector body 200, and nests within the helical groove 246 of the drive body 202. With this engagement, the locking body 262 prevents longitudinal movement of the sheath connector body 200 (and thus the delivery sheath assembly 42) relative to the drive body 202. Conversely, when the user interface body 260 is pivoted downwardly (relative to the orientation of FIG. 7), the locking body 262 is moved from engagement with the drive body 202, thereby permitting sliding movement of the sheath connector body 200 relative to the drive body 202. In other words, retraction of the delivery sheath assembly 42 from the delivery or loaded state to the deployed state can be accomplished by a user pressing downwardly on the user interface body 260 to release the locking body 262, and then retracting (e.g., sliding in the proximal direction) the user interface body 260 relative to the housing 180. With this operation, the delivery sheath assembly 42 will retract or slide relative to the inner shaft assembly 44 and the outer stability tube 52. When the pressing force is removed, the biasing device 264 operates to move the locking body 262 back into nested engagement with the helical groove 246 of the drive body 202. Advancement of the delivery sheath assembly 42 can be achieved in a similar manner, with the user simply releasing the locking body 262 as described above, and then moving the user interface body 260 forwardly relative to the housing 180.

In addition to the coarse movement described above, with the actuator assembly 204 in the locked state (i.e., the locking body 262 (FIG. 6) engaged with the exterior threads 246 of the drive body 202), fine tuned movement of the delivery sheath assembly 42 can be achieved by the user rotating the control knob 244. Rotation of the drive body 202 is transferred onto the locking body 262 via interface within the helical groove 246. As the locking body 262 rides within the helical groove 246, a force is applied to the user interface body 260, and thus to the sheath connector body 200. As a result, rotation of the drive body 202 in a first direction causes the delivery sheath assembly 42 to slightly retract, whereas rotation in an opposite direction causes the delivery sheath assembly 42 to slightly advance. Alternatively, a wide variety of other constructions can be employed for the actuator mechanism 182 that facilitate user-caused retraction (and optionally advancement) of the delivery sheath assembly 42.

During use, the delivery device 40 is initially loaded with a stented prosthetic heart valve as described above. For example, FIGS. 9A and 9B illustrate, in simplified form, a distal portion of a heart valve restoration system 350 in accordance with principles of the present disclosure, including the stented prosthetic heart valve 30 loaded within the delivery device 40. As a point of reference, the system 350 is in a delivery condition in FIGS. 9A and 9B, with the delivery device 40 arranged in the delivery or loaded state. The prosthetic heart valve 30 is crimped over the inner shaft assembly 44 to engage the engagement structure 110. The capsule 50 compressively contains the prosthesis 30 in the compressed arrangement. Finally, the stability tube 52 is coaxially arranged over the shaft 60 of the delivery sheath assembly 42, with the distal end 140 located proximal the proximal end 70 of the capsule 50. The delivery device 40 is then manipulated to deliver the compressed prosthetic heart valve 30 to the heart valve to be repaired. Once positioned, the capsule 50 is retracted via operation of the actuator mechanism 182 (FIG. 6), thereby permitting the prosthetic heart valve 30 to self-expand and deploy. In some embodiments, prior to full deployment the prosthetic heart valve 30, the capsule 50 can be advanced back over the prosthetic heart valve 30 for permitting movement to a new location. The delivery devices shown and described herein can be modified for delivery of balloon-expandable stented heart valves, within the scope of the present disclosure. That is to say, delivery of balloon-expandable stented heart valves can be performed percutaneously using modified versions of the delivery devices of the present disclosure. In general terms, this includes providing the transcatheter delivery assembly akin to those described above, along with a balloon catheter and a guide wire.

Figure 10A:
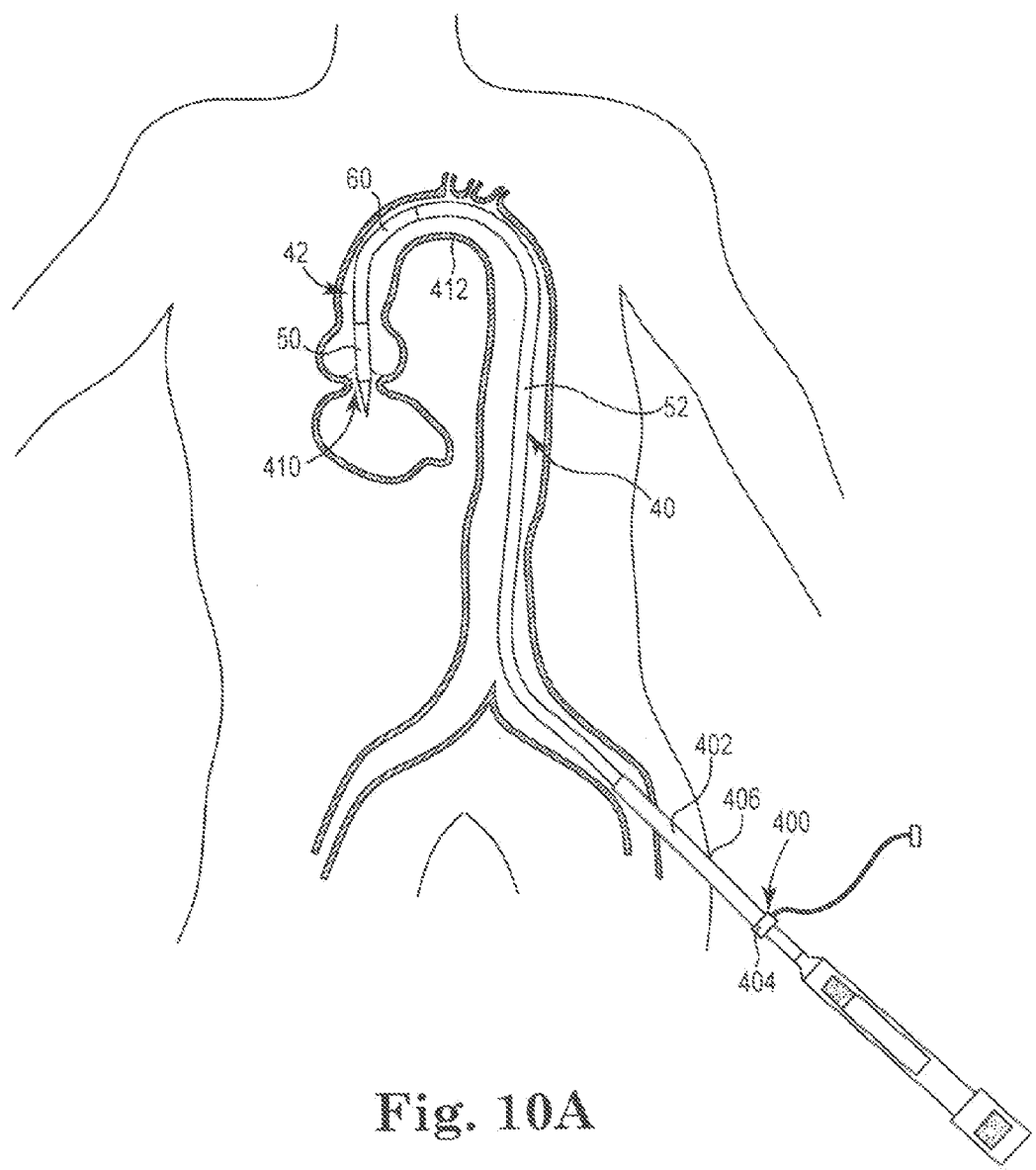
FIGS. 10A and 10B illustrate various steps of a method for replacing or repairing a defective heart valve of a patient in accordance with principles of the present disclosure.

In some embodiments, the delivery device 40 can be used in conjunction with an introducer device 400 as shown in FIG. 10A. Introducer devices 400 are known in the art, and generally include an introducer sheath 402 and a valve 404. The introducer sheath 402 is typically a resilient body. To access a bodily lumen (e.g., femoral artery) of the patient, an incision 406 is formed in the patient's skin, and the introducer sheath 402 inserted through the incision and into the desired bodily lumen. The valve 404 fluidly closes the connection with the bodily lumen external the patient. The delivery device 40 is then inserted into the bodily lumen via the introducer device 400. As generally reflected in FIG. 10A, for example, the introducer sheath 402 has an inner diameter greater than that of the outer stability tube 52 (as well as the capsule 50), such that the capsule 50 can readily be delivered through the bodily lumen, directed to other branches of the patient's vasculature, and then to the defective heart valve implantation site 410 (e.g., aortic heart valve). In this regard, the introducer valve 404 frictionally contacts the outer stability tube 52, thereby establishing a low friction hemostasis seal around the outer stability tube 52. Notably, however, the outer stability tube 52 isolates the delivery sheath assembly 42 (and in particular the shaft 60) from the introducer sheath 402 and valve 404. Stated otherwise, while the outer stability tube 52 is in physical contact with portions of the introducer device 400, the delivery sheath assembly 42 does not directly contact the introducer device 400. Further, the stability tube 52 overtly supports the delivery shaft 60 in traversing the tortuous vasculature, minimizing occurrences of kinks forming in the shaft 60 when, for example, moving across the aortic arch 412.

Figure 10B:
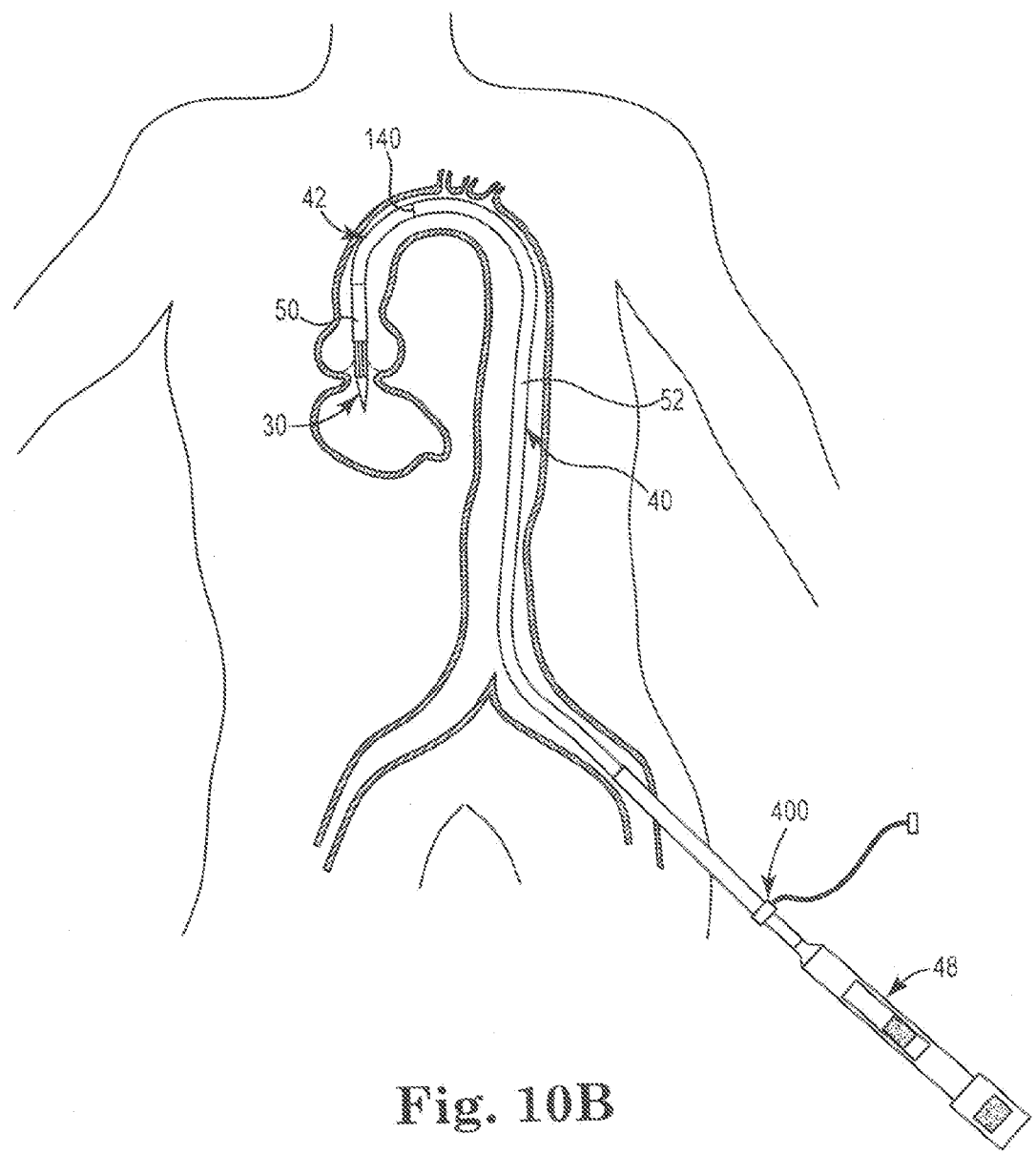

With reference to FIG. 10B, to deploy the prosthetic heart valve 30 (drawn schematically in FIG. 10B) from the delivery device 40, the handle 48 is operated to distally retract the delivery sheath assembly 42. In particular, the capsule 50 (hidden in FIG. 10B) is withdrawn from over the prosthetic heart valve 30, thereby permitting the prosthetic heart valve 30 to self-deploy from the delivery device 40. In this regard, due to the presence of the stability tube 52, with transitioning of the delivery device 40 from the delivery state to the deployment state via sliding of the delivery sheath assembly 42, the delivery sheath assembly 42 does not bear against or otherwise frictionally interface with the introducer device 400. As a result, unlike previous percutaneous delivery procedures, the clinician and/or an assistant are not required to carefully monitor spacing between a handle 48 and the introducer device 400 while constantly correcting for any discrepancies as no frictional interface is established during retraction of the delivery sheath assembly 42. Further, because the distal end 140 of the stability tube 52 is in close proximity to the capsule 50, an overall stabilization of the delivery sheath 42 during retraction thereof is provided.

Figure 11A:
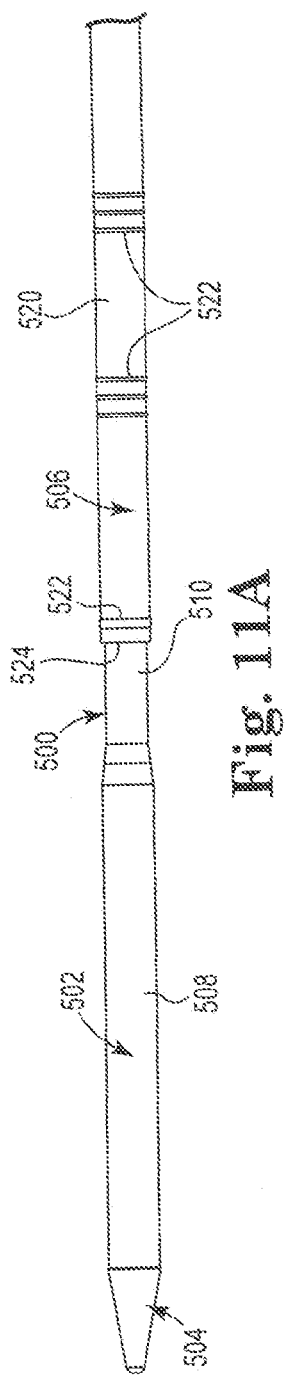
FIG. 11A is a simplified side view of a distal portion of another system, including an alternative delivery device in accordance with principles of the present disclosure in a delivery state.

While the delivery device 40 has been described as spatially affixing the stability tube 52 relative to the inner shaft assembly 44 (FIG. 3) via the handle 48 (i.e., the delivery sheath assembly 42 is movable relative to the stability tube 52, but not vice-versa), other constructions are also envisioned. For example, the handle 48 can be configured to provide a second actuator mechanism that permits a user to longitudinally move the stability tube 52 relative to the delivery sheath assembly 42 and the inner shaft assembly 44, for example to effectuate re-capture or re-sheathing of a partially deployed prosthetic heart valve. For example, FIG. 11A illustrates a distal portion of an alternative delivery device 500 that includes a delivery sheath assembly 502, an inner shaft assembly 504 (referenced generally), and a stability tube 506. Though not shown, the components 502-506 are proximally maintained by a handle. The handle is akin to the handle to the handle 48 (FIG. 3) described above, and provides at least two actuator mechanisms; a first actuator mechanism configured to effectuate user-caused movement of the delivery sheath assembly 502 relative to the inner shaft assembly 504 and the stability tube 506, and a second actuator mechanism configured to effectuate user-caused longitudinal movement of the stability tube 506 relative to the delivery sheath assembly 502 and the inner shaft assembly 504.

The delivery sheath assembly 502 can incorporate any of the constructions described above, and can be akin to the delivery sheath assembly 42 (FIG. 3). Thus, for example, the delivery sheath assembly 502 can include a distal capsule 508 and a proximal shaft 510. As with previous embodiments, the capsule 508 is configured to compressively contain a stented percutaneous heart valve (not shown), with the shaft 510 connecting the capsule 508 to the handle (not shown). The inner shaft assembly 504 can similarly assume any of the constructions described above, and thus can be akin to the inner shaft assembly 44 (FIG. 3). In more general terms, then, the inner shaft assembly 504 incorporates or includes one or more engagement features (not shown) configured to releasably engage the stented prosthetic heart valve otherwise disposed within the capsule 508.

The stability tube 506 is akin to the stability tube 52 (FIG. 3) described above, and includes a tubular body 520 and one or more support elements 522 (referenced generally). The tubular body 520 can be a surgically safe, circumferentially flexible sheath (e.g., a polymer catheter) sized to be slidably received over the delivery sheath shaft 510. The tubular body 520 terminates at distal end 524. In some constructions, a longitudinal cut (not shown) can be formed along the tubular body 520 to permit circumferential expansion as described below. Alternatively, the tubular body 520 can be uniform. The support members 522 circumferentially reinforce the tubular body 520 in a manner permitting elastic radial expansion. For example, the reinforcement members 522 can be a series of coil springs. The reinforcement members 522 can be formed over the tubular body 520, or can be embedded within a thickness thereof. In other embodiments, the reinforcement members 522 can be embedded Nitinol zigs, coils, or other elastic elements.

In the delivery state of FIG. 11A, the capsule 508 compressively retains the stented prosthetic heart valve (hidden in the view of FIG. 11A) in a compressed arrangement over the inner shaft assembly 504. The distal end 524 of the stability tube 506 is located proximal the capsule 508. The delivery device 500 can then be manipulated as described above to percutaneously deliver the stented prosthetic heart valve, in the compressed arrangement, to the heart valve to be restored.

Figure 11B:
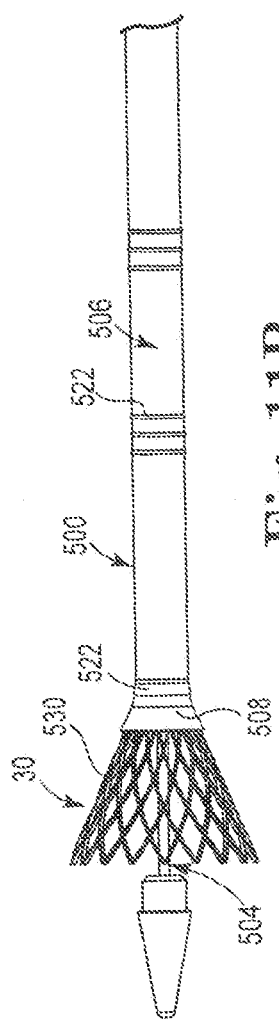
FIG. 11B is a simplified side view of the system of FIG. 11B in a partial deployment condition.

The delivery sheath assembly 502 can then be retracted as described above to release the stented prosthetic heart valve (hidden in the view of FIG. 11A) from the confines of the capsule 508. In some embodiments, the clinician may desire to only partially release the stented prosthetic heart valve from the delivery device 500 and then evaluate a position relative to the implantation site. For example, FIG. 11B illustrates the delivery device 500 in a partially deployed state, with the capsule 508 being partially retracted from the stented prosthetic heart valve 30. As shown, a distal region 530 of the prosthesis 30 is exposed relative to the capsule 508, and has self-expanded toward the natural, expanded arrangement. A proximal region (hidden in FIG. 11B) remains within the capsule 508 and coupled to the inner shaft assembly 504. In the partially-deployed state of FIG. 11B, then, the clinician can evaluate a position of the stented prosthetic heart valve 30 prior to full release or deployment from the delivery device 500.

Under circumstances where the clinician determines that the prosthetic heart valve 30 should be repositioned, a recapturing procedure is performed. In particular, the stability tube 506 is distally advanced over the capsule 508 and the distal region 530 of the stented prosthetic heart valve 30. As shown, the reinforcement members 522 provide necessary circumferential support to the tubular member 520, thereby facilitating recapturing (and re-compressing) of the distal region 530.

Figure 11C:
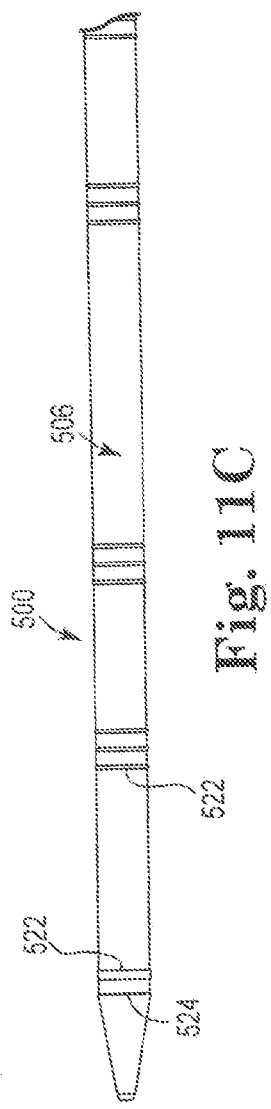
FIG. 11C is a simplified side view of the system of FIG. 11A in a re-captured condition.

FIG. 11C illustrates the delivery device 500 in a re-captured state, with the stability tube 506 disposed over, and thus compressing, the previously-deployed distal region 530 (FIG. 11B) of the stented prosthetic heart valve 30 (FIG. 11B). In other words, the distal end 524 of the stability tube 506 is now distal the prosthetic heart valve 30. Under circumstances where the reinforcement members 522 are sufficient to cause the diameter of the distal end 524 to return approximately to the initial diameter of the capsule 508 (FIG. 11A), the delivery sheath assembly 502 (FIG. 11A) can be driven retrograde back through the stenotic valve. Conversely, if the distal end 524 of the stability tube 506 does not return to the initial diameter of the capsule 508, the delivery sheath assembly 502 (FIG. 11A) can be driven distally to completely re-sheath the stented prosthetic heart valve 30. Once the prosthetic heart valve 30 (in the compressed arrangement) has been desirably repositioned, full deployment can be effectuated as described above.

The stented prosthetic heart valve delivery devices and methods of the present disclosure provide a marked improvement over previous designs. By isolating the delivery sheath from the introducer device, potential complications associated with previous configurations are overcome.

Although the present disclosure has been described with reference to preferred embodiments, workers skilled in the art will recognize that changes can be made in form and detail without departing from the spirit and scope of the present disclosure.

What is claimed is:

1. A delivery device for percutaneously delivering a stented prosthetic heart valve, the prosthetic heart valve being radially self-expandable from a compressed arrangement to a normal, expanded arrangement, the delivery device comprising:
a delivery sheath assembly defining a lumen and including a distal capsule and a shaft proximal the distal capsule, wherein the capsule is configured to compressively contain an entire length of the prosthetic heart valve;
a handle including:
a housing defining a proximal side and a distal side,
an actuator mechanism maintained by the housing and coupled to the shaft such that the shaft extends distal the distal side, wherein the actuator mechanism is configured to selectively move the shaft relative to the housing; and
an outer stability tube coupled to the housing and coaxially received over the shaft such that the shaft is slidable relative to the outer stability tube, wherein a distal end of the outer stability tube is proximal the capsule;
wherein the outer stability tube extends over at least a majority of the shaft in distal extension from the distal side of the housing;
and further wherein a rigidity of the capsule is greater than a rigidity of the outer stability tube;
and further wherein the actuator mechanism is operable to transition the delivery device from a delivery state in which the capsule encompasses an entire length of the prosthetic heart valve and a distal end of the outer stability tube is proximal the capsule to a deployed state in which the capsule is withdrawn from the prosthetic heart valve, the shaft sliding relative to the outer stability tube when transitioning from the delivery state to the deployed state.

2. The delivery device of claim 1, wherein the outer stability tube is configured to isolate the delivery sheath assembly from a separate introducer valve component through which the delivery device is inserted into a patient.

3. The delivery device of claim 1, further comprising:
a retention member disposed within the lumen and configured to support the prosthetic heart valve within the capsule in the delivery state.

4. The delivery device of claim 3, wherein the retention member is coupled to the housing such that the capsule slides relative to the retention member in transitioning from the delivery state to the deployed state.

5. The delivery device of claim 1, further comprising:
a flush port construction maintained by the housing and including tubing fluidly connected to a region between an outer diameter of the delivery sheath assembly and an inner diameter of the outer stability tube.

6. The delivery device of claim 1, wherein an outer diameter of the capsule is greater than an outer diameter of the shaft, the shaft being affixed to the capsule at a connection point, and further wherein in the delivery state, the connection point is distal the distal end of the outer stability tube by a distance in the range of 3-13 cm.

7. The delivery device of claim 1, wherein an outer diameter of the capsule is greater than an outer diameter of the shaft, the capsule being affixed to the shaft at a connection point, and further wherein in the deployed state, the connection point is distal the distal end of the outer stability tube.

8. The delivery device of claim 1, wherein the shaft is a braided tube and the capsule has a construction differing from that of the shaft.

9. The delivery device of claim 1, wherein the outer stability tube includes:
a tubular body; and
reinforcing members circumferentially supporting the tubular body;
wherein the outer stability tube is moveable relative to the delivery sheath assembly for performing a re-capture operation.

10. A system for restoring a defective heart valve of a patient, the system comprising:
a delivery device including:
an outer stability tube defining a distal end,
a delivery sheath assembly defining a lumen and including a distal capsule and a shaft proximal the capsule, the shaft slidably received within the outer stability tube,
a handle including:
a housing defining a distal side and coupled to the outer stability tube such that the outer stability tube extends distal the distal side,
an actuator mechanism maintained by the housing and coupled to the shaft such that the delivery sheath assembly extends distal the distal side and is selectively moveable relative to the outer stability tube with operation of the actuator mechanism;
wherein the outer stability tube extends over at least a majority of the shaft in distal extension from the distal side of the housing;
and further wherein a rigidity of the capsule is greater than a rigidity of the outer stability tube; and
a prosthetic heart valve having a stent frame and a valve structure attached to the frame and forming at least two valve leaflets, the prosthetic heart valve being self-expandable from a compressed arrangement to a natural arrangement;
wherein the system is configured to be transitionable from a loaded condition in which an entire length of the prosthetic heart valve is retained within the capsule and the outer stability tube is distal the capsule, and a deployed condition in which the capsule is withdrawn from the prosthetic heart valve to permit the prosthetic heart valve to self-expand to the natural arrangement and release from the delivery device, the actuator mechanism being configured to effectuate transitioning from the loaded condition to the deployed condition by sliding the delivery sheath assembly relative to the prosthetic heart valve and the outer stability tube.

11. The system of claim 10, further comprising:
an introducer device including an introducer sheath and a valve, the introducer device configured to establish hemostasis with the outer stability tube, the outer stability tube isolating the shaft from the introducer device.

12. The system of claim 10, further comprising:
a retention member disposed within the lumen and configured to support the prosthetic heart valve within the capsule in the loaded condition.

13. The system of claim 12, wherein the retention member is coupled to the housing such that the capsule slides relative to the retention member in transitioning from the loaded condition to the deployed condition.

14. The system of claim 10, further comprising:
a flush port construction maintained by the housing and including tubing fluidly connected to a region between an outer diameter of the delivery sheath assembly and an inner diameter of the outer stability tube.

15. The system of claim 10, wherein an outer diameter of the capsule is greater than an outer diameter of the shaft, the shaft being affixed to the capsule at a connection point, and further wherein in the loaded condition, the connection point is distal the distal end of the outer stability tube by a distance of 3-13 cm.

16. The system of claim 10, wherein an outer diameter of the capsule is greater than an outer diameter of the shaft, the capsule being affixed to the shaft at a connection point, and further wherein in the deployed condition, the connection point is distal the distal end of the outer stability tube.

17. The system of claim 10, wherein the shaft is a braided tube and the capsule has a construction differing from that of the shaft.

18. The system of claim 10, wherein the outer stability tube includes:
a tubular body; and
reinforcing members circumferentially supporting the tubular body;
wherein the outer stability tube is moveable relative to the delivery sheath assembly for performing a re-capture operation.

19. The delivery device of claim 1, wherein the capsule includes a laser-cut metal tube and the outer stability tube is a polymer catheter.

* * * * *